United States Patent [19]

Cates

[11] 3,992,373

[45] Nov. 16, 1976

[54] PHOSPHOROTHIOAMIDES

[75] Inventor: Lindley A. Cates, Houston, Tex.

[73] Assignee: Research Corporation, New York, N.Y.

[22] Filed: Dec. 13, 1974

[21] Appl. No.: 532,376

Related U.S. Application Data

[60] Continuation of Ser. No. 180,509, Sept. 14, 1971, abandoned, which is a division of Ser. No. 852,945, Aug. 25, 1969, Pat. No. 3,660,413.

[52] U.S. Cl. .......................... 260/239 EP; 424/200; 260/552 SC
[51] Int. Cl.² ............................................ C07F 9/56
[58] Field of Search ............................. 260/239 EP

[56] References Cited
UNITED STATES PATENTS 3,201,313   8/1965   Bardos et al. ................. 260/239 EP
3,660,413   5/1972   Cates ................................. 260/947

OTHER PUBLICATIONS

Cates, J. Med. Chem., vol. 10, pp. 924–927, (1967).

Kerkach et al., Chem. Abstracts, vol. 59, Abstract No. 12669d, (1963).

*Primary Examiner*—Alton D. Rollins
*Attorney, Agent, or Firm*—Dennis P. Clarke; Harold L. Stowell

[57] ABSTRACT

Antibacterial phosphorothioamides are prepared by the reaction of phosphorothiocyanates with hydrazine or hydrazides.

1 Claim, No Drawings

PHOSPHOROTHIOAMIDES

The invention described herein was made in the course of work under a grant or award from the Department of Health, Education and Welfare.

This is a continuation of application Ser. No. 180,509, filed Sept. 14, 1971, and now abandoned, which was a division of application Ser. No. 852,945, filed Aug. 25, 1969, now U.S. Pat. No. 3,660,413.

This invention relates to novel phosphorothioamide compounds exhibiting antibacterial activity.

The phosphorothioamide compounds of the invention are of the general formula $(RO)_2PONHCSY$, $ROPO(NHCSY)_2$ and $PO(NHCSY)_3$ wherein Y is H, $N(CH_2)_2$, $NHNHC_6H_5$, NHNHCOOR or $NHNHCOC_5H_4N$ and R is lower alkyl. As used herein, the term "lower alkyl" embraces alkyl radicals, branched or straight-chain, having 1–4 carbon atoms inclusive, e.g., methyl, ethyl, propyl, isopropyl and the butyls.

The phosphorothioamide compounds of the invention are generally prepared by the reaction, usually condensation, of a phosphorothiocyanate with a hydrazine or hydrazide. The reaction is usually effected in the presence of an inert solvent, e.g., ether or carbon tetrachloride, in the cold by adding a solution of one of the reactants to the other dissolved in the same solvent chilled to about 5°–10° C. The product generally precipitates from the reaction mixture but can also be recovered by evaporation of the product. The crude product is purified by solvent recrystallization, e.g., ether-alcohol.

Representative compounds of the invention were screened against three gram-positive and gram-negative microorganisms using the agar diffusion-filter paper disc method and found to exhibit significant antibacterial activity.

EXAMPLE 1. $(C_2H_5O)_2PONHCHS$

To a chilled solution of diethyl phosphoroisothiocyantidate $(C_2H_5O)_2PONCS$, Can. J. Chem., 37, 525 (1959), dissolved in chilled ether was gradually added an equimolar quantity of hydrazine dissolved in the same solvent. After separation and recrystallization, the $(C_2H_5O)_2PONHCHS$ product melted 129° C with decomposition.

Reduction of the phosphoroisothiocyantidate reactant and the same product was obtained when 4-methyl-3-thiosemicarbazide was substituted for hydrazine.

EXAMPLE 2. $(C_2H_5O)_2PONHCSNHNHC_6H_5$

Using the procedure of the previous example, phenylhydrazine was condensed with diethyl phosphoroisothiocyantidate to give $(C_2H_5O)_2PONHCSNHNHC_6H_5$ melting 125° C with decomposition.

Similar products are obtained when phenylhydrazine bearing substituents such as alkyl, halo, alkoxy and the like on the phenyl ring is substituted for phenylhydrazine.

EXAMPLE 3. $(C_2H_5O)_2PONHCSNHNHCOOC_2H_5$

Using the procedure of the previous examples, ethyl carbazate $H_2NNHCOOC_2H_5$ was condensed with diethyl phosphoroisothiocyantidate to give $(C_2H_5O)_2PONHCSNHNHCOOC_2H_5$ melting 147° C with decomposition.

EXAMPLE 4. $(C_2H_5O)_2PONHCSNHNH-4-COC_5H_4N$

Using the procedure of the previous examples, but no solvent, pyridine-4-carboxylic acid hydrazide $H_2NNH-4-COC_5H_4N$ was condensed with diethyl phosphoroisothiocyantidate to give $(C_2H_5O)_2PONHCSNHNH-4-COC_5H_4N$ melting 147° C with decomposition.

EXAMPLE 5. $C_2H_5OPO(NHCSNHNHCOOC_2H_5)_2$

To a chilled solution of ethyl phosphorodiisothiocyantidate $C_2H_5OPO(NCS)_2$, Saunders et al., J. Chem. Soc., 699 (1948), dissolved in chilled ether was gradually added a solution containing twice the equimolar quantity of ethyl carbazate. Unlike the other examples, 1 hour's heating at 35° C was required to complete the reaction. After separation and recrystallization, the $C_2H_5OPO(NHCSNHNHCOOC_2H_5)_2$ product decomposed about 80° C before melting.

EXAMPLE 6. $C_2H_5OPO(NHCSNHNH-4-COC_5H_4N)_2$

Using the procedure of the previous example, but acetonitrile as the solvent, pyridine-4-carboxylic acid hydrazide was added to ethyl phosphorodiisothiocyantidate to give $C_2H_5OPOCNHCSNHNH-4-COC_5H_4N$ decomposing about 105° C before melting.

EXAMPLE 7. $C_2H_5OPO(NHCSNHNH-COOC_2H_5)(NHCSNHNHC_6H_5)$

Following the general procedure, equimolar quantities of phenylhydrazine and ethyl carbazate were sequentially added to a solution of ethyl phosphorodiisothiocyantidate to give $C_2H_5OPO(NHCSNHNH-COOC_2H_5)(NHCSNHNHC_6H_5)$ which separated as a yellow oil before solidifying. The solid decomposed about 65° C before melting.

EXAMPLE 8. $C_2H_5OPO(NHCHS)[NHCSN(CH_2)_2]$

Essentially following the procedure of the previous example, ethanethiol and then aziridine were added to ethyl phosphorodiisothiocyantidate in ether. Reduction followed by condensation gave $C_2H_5OPO(NHCHS)[NHCSN(CH_2)_2]$ which decomposed about 147° C before melting.

EXAMPLE 9. $PO(NHCSNHNHCOOC_2H_5)_3$

To a chilled solution of phosphinylidyne triisothiocyanate $PO(NCS)_3$, Saunders et al, J. Chem. Soc., 699 (1948) dissolved in chilled ether was gradually added a solution containing triple the equimolar quantity of ethyl carbazate. After separation and recrystallization, the $PO(NHCSNHNHCOOC_2H_5)_3$ product decomposed about 53° C before melting.

In general, all of the products described were analyzed for and gave satisfactory C, H and N analyses. Infrared spectra of the products on a Beckman spectrophotometer gave the expected absorptions. All products decomposed on melting or decomposed over a wide range before melting.

The antibacterial spectra were determined by saturating 12.7 mm filter paper discs with 2 drops of an aqueous of alcoholic solution or suspension of the compound (20 mg/ml) and placing these on nutrient agar seeded with 48-hour nutrient culture broths of the test organisms (0.5 ml). The zones of inhibition around the discs were measured after 4 days of incubation at 37° C. The first value given in the table below is the zone of complete inhibition; the value in parentheses which follows is the zone of complete and partial inhibition also in millimeters.

| Compound | Solvent | M. smegmatis | S. aureus | γ-Strep. | E. coli | P. vulgaris | Ps. aeruginosa |
|---|---|---|---|---|---|---|---|
| 1 | EtOH | 25 (35) | | | | | |
| 1 | H$_2$O | 17 (25) | | | | | |
| 2 | EtOH | 25 (33) | 20 | 24 | | | |
| 4 | EtOH | 42 (54) | 19 | 20 | 18 (22) | 19 | 19 |
| 5 | H$_2$O | 15 (21) | 20 | | | | |
| 6 | H$_2$O | 36 (39) | | | | | |
| 7 | EtOH | 18 | 17 | | | | 15 |
| 9 | H$_2$O | 19 | 18 | | | | 15 |

I claim:
1. C$_2$H$_5$OPO(NHCHS) [NHCSN(CH$_2$)$_2$].

* * * * *